United States Patent
Reddy et al.

(10) Patent No.: US 6,836,528 B2
(45) Date of Patent: Dec. 28, 2004

(54) METHODS AND APPARATUS FOR DETECTING STRUCTURAL, PERFUSION, AND FUNCTIONAL ABNORMALITIES

(75) Inventors: Shankara B. Reddy, Cedarburg, WI (US); Gopal B. Avinash, New Berlin, WI (US); Xiaoye Wu, Rexford, NY (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/602,806

(22) Filed: Jun. 24, 2003

(65) Prior Publication Data

US 2004/0066881 A1 Apr. 8, 2004

Related U.S. Application Data

(60) Provisional application No. 60/398,151, filed on Jul. 23, 2002.

(51) Int. Cl.$^7$ .............................................. A61B 6/03
(52) U.S. Cl. .............................. 378/5; 378/8; 378/901
(58) Field of Search ................................ 378/4, 5, 8, 15, 378/16, 901

(56) References Cited

U.S. PATENT DOCUMENTS

| | | | |
|---|---|---|---|
| 6,033,645 A | 3/2000 | Unger et al. | |
| 6,231,834 B1 | 5/2001 | Unger et al. | |
| 6,299,857 B1 | 10/2001 | Elmaleh et al. | |
| 6,358,208 B1 | 3/2002 | Lang et al. | |
| 6,521,211 B1 | 2/2003 | Unger et al. | |
| 6,671,541 B2 | 12/2003 | Bishop et al. | |
| 2003/0215120 A1 * | 11/2003 | Uppaluri et al. | 382/128 |
| 2004/0101090 A1 * | 5/2004 | Drummond et al. | 378/4 |

* cited by examiner

*Primary Examiner*—David V Bruce
(74) *Attorney, Agent, or Firm*—Carl B. Horton, Esq.; Armstrong Teasdale LLP

(57) ABSTRACT

A method includes scanning myocardial tissue of a patient with an Energy Discrimination Computed Tomography (EDCT) system to acquire data, and analyzing the acquired data for at least one of cardiac measurements, diagnosis, and prognosis after interventions.

20 Claims, 5 Drawing Sheets

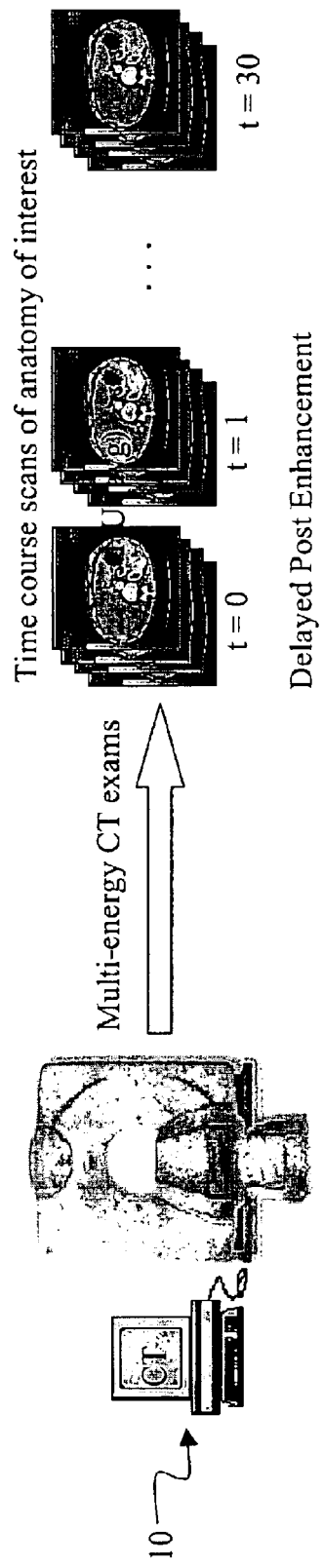
FIG. 5
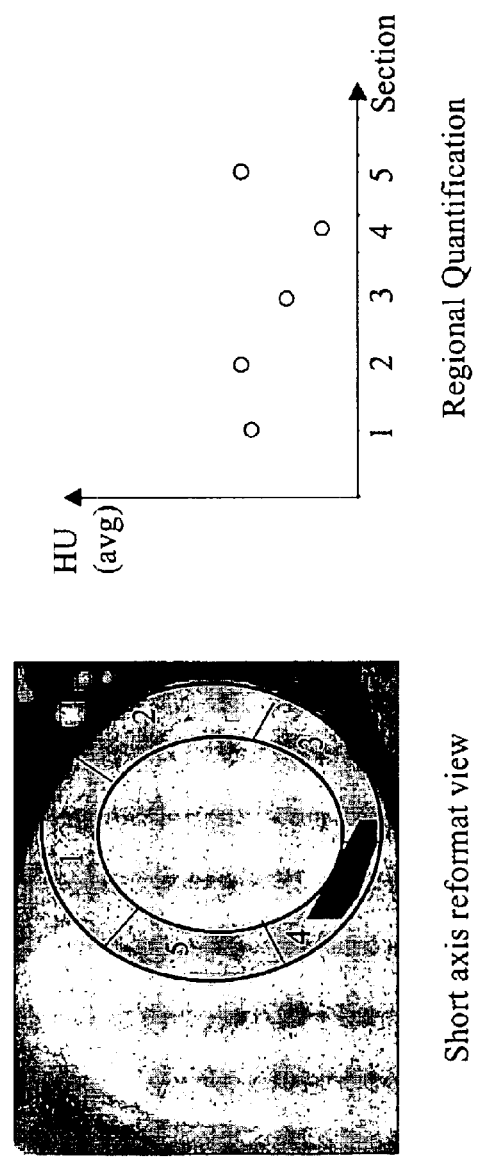
FIG. 6 Result of energy discrimination analysis on multi-energy CT images to identify perfusion defects in myocardial tissue

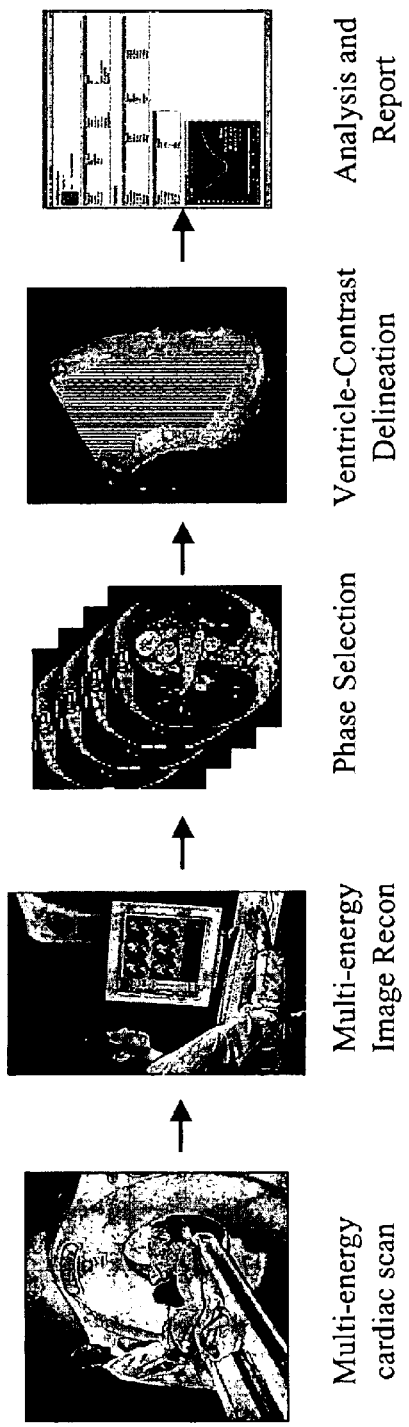

FIG. 7 System for acquisition and analysis of multi-energy CT exams for cardiac function analysis.

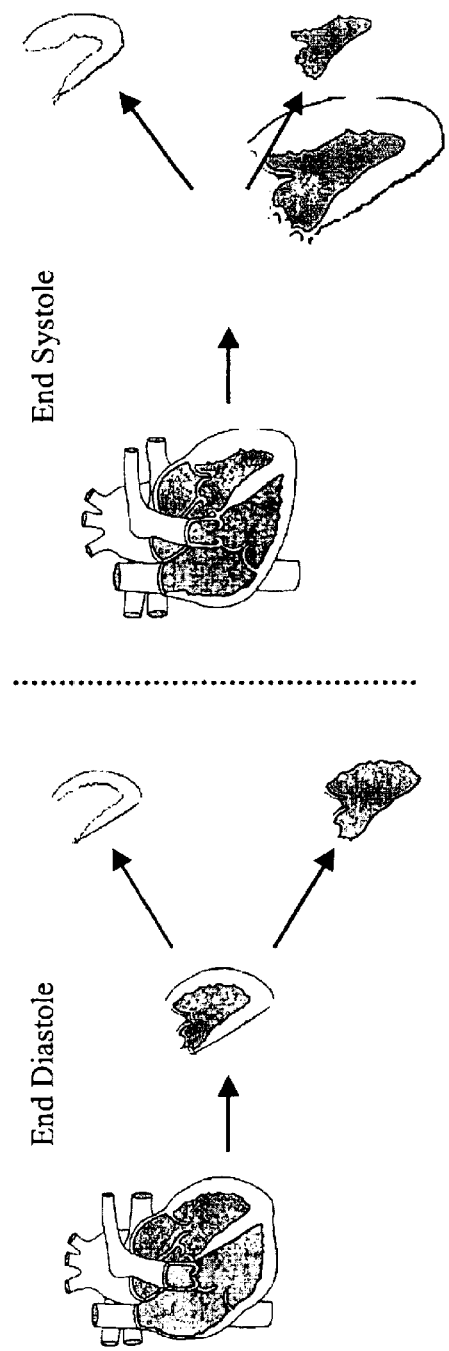

FIG. 8 Results of delineation of the ventricular myocardium from the contrast-filled blood using multi-energy CT scans. First, each of the ventricles is separated from the surrounding anatomy (example shows left ventricle separation), followed by separation of contrast-filled blood from the ventricular tissue. This is done at both end diastole and end systole.

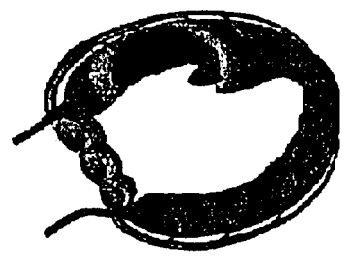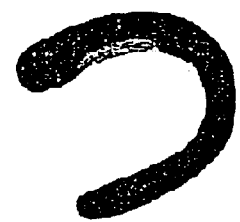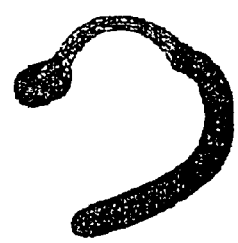
FIG. 9 Examples of accurate diagnoses by energy discrimination analysis on multi-energy CT exams. a. Transmural infarction; b. Sub-endocardial infarction; c. Hypertrophic cardiomyopothy; d. Myocardial ischemia and injury.

US 6,836,528 B2

METHODS AND APPARATUS FOR DETECTING STRUCTURAL, PERFUSION, AND FUNCTIONAL ABNORMALITIES

CROSS REFERENCE TO RELATED APPLICATIONS

This application claims the benefit of U.S. provisional application No. 60/398,151 filed Jul. 23, 2002, which is hereby incorporated by reference in its entirety.

BACKGROUND OF THE INVENTION

This invention relates to computed tomographic (CT) imaging, and more particularly to methods and apparatus for the detection and diagnosis of abnormalities related to two forms of heart disease, namely, ischemic heart disease and abnormalities in the structure of the heart's muscle and valves.

In spite of recent advancements in CT technology (faster scanning speed, larger coverage with multiple detector rows), energy resolution is still a missing piece, namely, wide x-ray photon energy spectrum from the x-ray source and the lack of energy resolution from CT detection systems. X-ray attenuation through a given object is not a constant. It is strongly dependent on the x-ray photon energy. This physical phenomenon shows in the image as a beam-hardening artifact: such as non-uniformity, shading and streaking. Some of them can be corrected, but some are much tougher to remove. In general, the common methods to deal with such problems are (1) water calibration, where each CT machine is carefully calibrated to remove beam-hardening from materials similar to water (2) iterative bone correction: where bones are separated in the first-pass image, then beam-hardening from bones are corrected in the second-pass. However, beam-hardening from materials other than water and bone, such as metal and contrast agent, become very difficult to correct. Even with the correction, conventional CT does not provide quantitative image values, instead, same material at different locations often shows different CT numbers.

The second drawback of the conventional CT is the lack of material characterization. For example, a highly attenuating material with low density can result in the same CT number in the image as a less attenuating material with high density. There is no insight into what the material is made of. Accordingly, the methods and apparatus described herein address the detection and diagnosis of abnormalities related to ischemic heart disease and abnormalities in the structure of the heart's muscle and valves.

BRIEF DESCRIPTION OF THE INVENTION

In one aspect, a method for obtaining data is provided. The method includes scanning myocardial tissue of a patient with an Energy Discrimination Computed Tomography (EDCT) system to acquire data, and analyzing the acquired data for at least one of cardiac measurements, diagnosis, and prognosis after interventions.

In another aspect, an Energy Determination Computed Tomography (EDCT) System includes a radiation source, a radiation detector, and a computer coupled to the radiation source and the radiation detector. The computer is configured to acquire data regarding a first energy spectrum of a scan of myocardial tissue of the patient, acquire data regarding a second energy spectrum of the scan, and analyze the acquired data for at least one of cardiac measurements, diagnosis and prognosis after interventions.

In yet another aspect, a computer readable medium encoded with a program is provided. The program is configured to instruct a computer to receive data regarding a first energy spectrum of a scan of myocardial tissue of the patient, receive data regarding a second energy spectrum of the scan, and analyze the acquired data for at least one of cardiac measurements, diagnosis and prognosis after interventions.

BRIEF DESCRIPTION OF THE DRAWINGS

FIG. 5 illustrates the Multi-energy CT system shown in FIGS. 1 and 2 used to acquire a time-delayed series of cardiac images to identify defects.

FIG. 6 illustrates that results of the analysis generate accurate measurements of the perfusion levels in different parts of the myocardium.

FIG. 7 illustrates one method for cardiac function measurement using a plurality of multi-energy CT exams.

FIG. 8 illustrates application of the multi-energy analysis outlined in FIGS. 3 and 4 to produce accurate delineation of the contrast-filled blood pool from the ventricular tissue.

FIG. 9 illustrates examples of diagnoses.

DETAILED DESCRIPTION OF THE INVENTION

Figure 1:
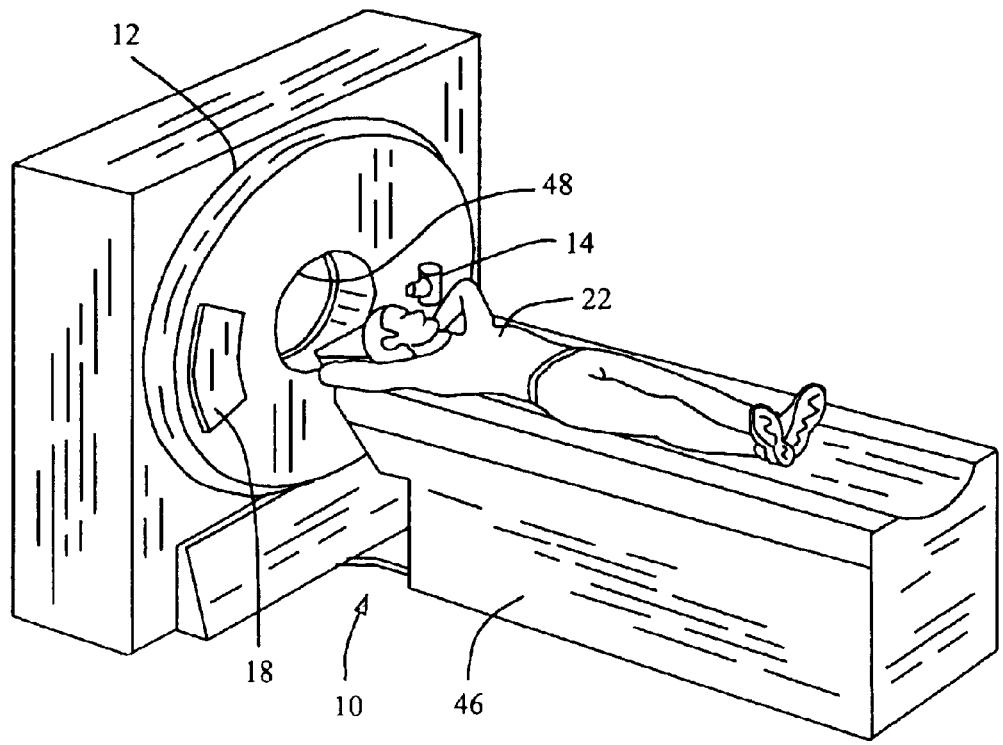
FIG. 1 is a pictorial view of a CT imaging system.

The methods and apparatus described herein address the detection and diagnosis of abnormalities related to two forms of heart disease, namely, ischemic heart disease and abnormalities in the structure of the heart's muscle and valves. Ischemic heart disease is a result of lack of adequate blood flow to myocardial tissue, generally due to stenosis of the coronary arteries. However, it manifests in perfusion defects and impaired cardiac function, specifically, reduced pumping efficiency of the ventricles (lower ejection fraction). Ischemic heart disease, particularly acute ischemia, if untreated within hours, can lead to severe consequences, including death. Early detection of ischemia and appropriate triage is important in managing a cardiac patient. Therefore, differentiation of healthy (normally perfused) tissue from ischemic and infarcted tissue is important to the survival of these patients. That is to quantify the levels of perfusion in different regions of the myocardium. Also of interest is to identify stunned (viable) myocardium that can be made revived by revascularization. At least some known diagnostic methods (e.g., Nuclear/PET, CT) provide some diagnostic information on ischemia in the form a perfusion map (Nuclear/PET or CT) or ST segment deviation (ECG). But, they do not provide direct association between the myocardial anatomy and the perfusion levels. Nor do they provide detailed information on the structure and/or viability of the myocardial tissue to help in optimal management of these patients. At least some known methods of measuring myocardial perfusion (e.g., Radionuclide imaging) provide a gross picture of myocardial ischemia but fail to provide detailed distribution and anatomic correlates of the myocardium.

Amongst the structural abnormalities the herein described methods and apparatus detect ventricular hypertrophy, hypertrophic cardiomyopathy, dilated cardiomyopathy and valvular defects, being the most common. High blood pressure is one cause of the structural abnormalities, particularly of ventricular hypertrophy and hypertrophic cardiomyopathy. These abnormalities manifest as structural changes in the myocardium at a molecular level. These structural changes reduce the effectiveness of the myocardium to contract and eject blood. They also affect the blood flow to the, myocardial tissue leading to further ischemia or infarction. Quantifying these structural changes is important for proper diagnosis of the conditions and effective management of the patients.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. Typically, the reconstructed images are represented by integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The helical weighting algorithms also scale the data according to a scaling factor, which is a function of the distance between the x-ray source and the object. The weighted data are then processed to construct an image that corresponds to a two dimensional slice taken through the object.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
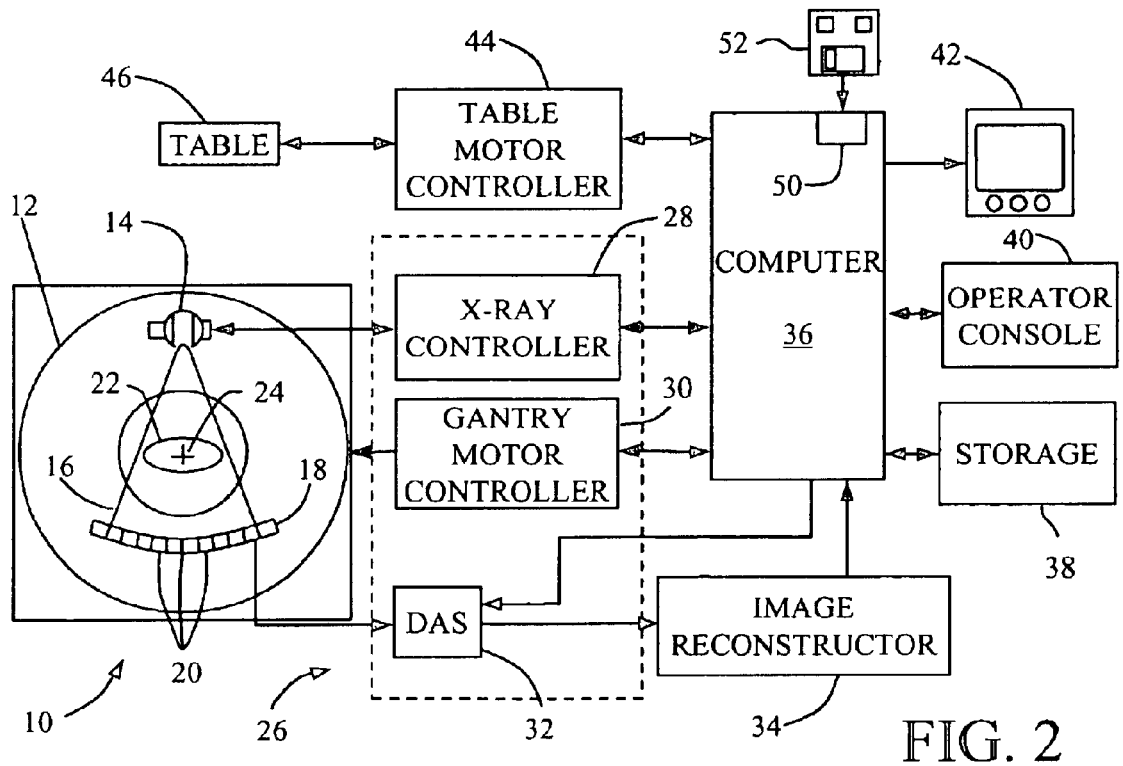
FIG. 2 is a block schematic diagram of the system illustrated in FIG. 1.

Referring to FIGS. 1 and 2, an Energy Discrimination multi-slice scanning imaging system, for example, an Energy Discrimination computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomographic (CT) system in that system 10 is configured to be responsive to different x-ray spectra.

Herein is described methods and apparatus for detecting structural, perfusion and functional abnormalities in myocardial tissue using energy-discriminating (also known as multi-energy) computed tomography (CT) system. First described is energy discriminating (multi-energy) CT system 10 and followed by cardiac applications of such a system 10 for a) detecting myocardial perfusion and defects and tissue viability, b) determining cardiac function, c) separation of soft/vulnerable plaque and calcified plaque from contrast agent in coronary arteries, d) detecting structural defects in heart muscle, and e) performing automated bone segmentation. Although the following description is given for a few representative examples, this method is equally applicable for other cardiac diagnostic applications.

Energy Discrimination (Multi-energy) CT System 10

Energy Discrimination CT (EDCT) system 10 can lessen or eliminate the problems associated with conventional CT (lack of energy discrimination and material characterization) altogether. In the absence of object scatter, system 10 separately detects two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes determine the x-ray attenuation (1) Compton scatter and (2) Photoelectric effect. In order to characterize the behavior of an object under x-ray attenuation, one only need to measure two independent parameters. Thus, detected signals from two energy regions provide enough information to use to resolve the energy dependence of the object being imaged.

The data analysis used in EDCT includes (1) Compton and photoelectric decomposition:

Instead of obtaining an overall attenuation coefficient as in conventional CT images, a pair of images is obtained in EDCT 10, separately presenting attenuations from Compton and photoelectric processes. Also, slight modifications can result in images representing effective Z and density.

(2) Basis material decomposition (BMD):

This method is based on the concept that the x-ray attenuation (in the energy region for medical CT) of any given material can be represented by a proper density mix of two other given materials. These two materials are called the Basis Materials. Through BMD, two CT images can be obtained, each presenting the equivalent density of one of the basis materials. Since density is independent of x-ray photon energy, these images are naturally free of beam-hardening artifacts. Meanwhile, one has the choice of choosing the basis material to target to a certain material of interest, thus enhancing the image contrast.

It should be noted that in order to optimize a dual energy CT system, the larger the spectra separation, the better the image quality. Also, the photon statistics in these two energy regions has to be close, otherwise, the poor statistical region will dominate the image noise.

There are different methods to obtain dual energy measurements. (1) Scan with two distinctive energy spectra. (2) Detect photon energy according to penetration depth at the detector. (3) Photon-counting. Photon counting provides clean spectra separation and an adjustable energy separation point for balancing photon statistics.

Cardiac Applications of Energy Discriminating Using Multi-energy CT System 10

Figure 3:
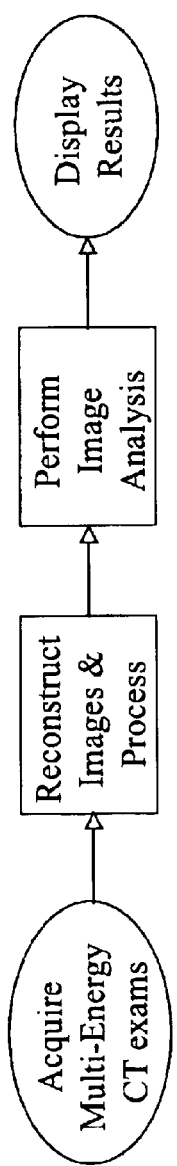
FIG. 3 illustrates general principles of one embodiment of a method using differences in attenuation properties of multi-energy X-rays in CT imaging to detect the abnormality, and quantify the severity and duration of a plurality of cardiac diseases.
Figure 4:
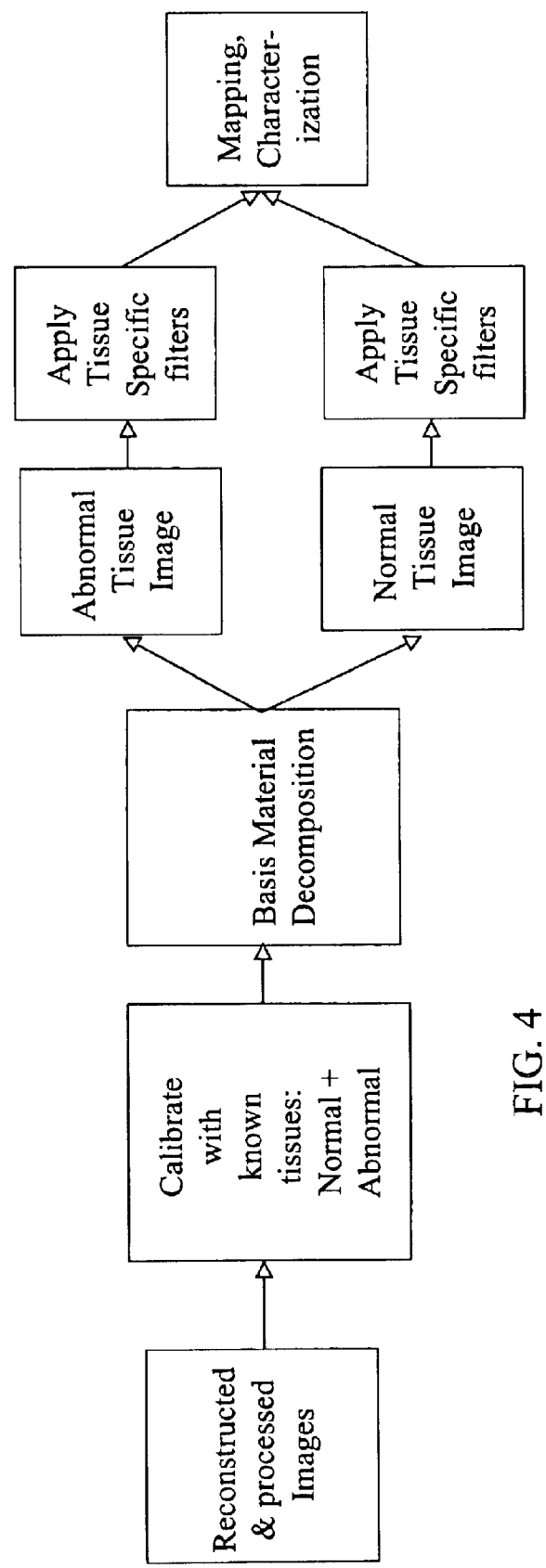
FIG. 4 illustrates an image analysis process.

Attenuation characteristics of different molecular structures and tissue densities in healthy and diseased myocardial tissue vary with the energy level of X-rays. In addition, attenuation characteristics of the contrast agent, soft/vulnerable plaque, calcified plaque and the bone also differ with X-ray energy level and they are different from the cardiac tissue. As a result, using different energy levels and applying the analysis described here will enable us to differentiate abnormal regions from normal ones and delineate the contrast, soft/vulnerable plaque, calcified plaque and bone from the cardiac tissue. One method described herein exploits these differences in attenuation properties to multi-energy X-rays in CT imaging to detect the abnormality, and quantify the severity and duration of these cardiac diseases. General principles of one embodiment here are illustrated in FIG. 3. While an Image analysis process is further illustrated in FIG. 4.

Reconstructed and processed multi-energy CT exams are calibrated with known tissues—normal and abnormal, contrast agents with different concentrations inside the cardiac tissue and bone segments. Calibrated images are decomposed into basis structures with known properties to partition them into normal and abnormal tissue. Same analysis is applied when separating bone, contrast agent, soft/vulnerable plaque and calcified plaque from cardiac tissue. These separated images are processed using tissue-specific filters. Results of these filters are further analyzed for characterization and diagnosis. They are also combined into suitable maps for visual presentation of the normal and abnormal regions. Representative examples of cardiac applications of energy discrimination on multi-energy CT systems are described below.

Detection of Perfusion Defects in Myocardial Tissue

When demand for blood by myocardial tissue exceeds the supply, the result is an ischemia (lack of oxygenated blood) of the myocardium. One common cause of myocardial ischemia is coronary stenosis. Localization of ischemia is the process of identifying of perfusion defects. Multi-energy CT system 10 is used to acquire a time-delayed series of cardiac images to identify such defects using a system 10 shown in FIG. 5. A plurality of images 70 are processed by energy discriminating system 10 illustrated in FIGS. 1 and 2 along with FIGS. 3 and 4. Results of the analysis would be accurate measurements of the perfusion levels in different parts of the myocardium as shown in FIG. 6.

Accurate Analysis of Cardiac Function

Cardiac function analyzes the pumping efficiency of the myocardial chambers, particularly of the ventricles. It includes measuring end-systolic and end-diastolic volumes in the ventricles, computing ejection fraction, stroke volume, and cardiac output. Another important aspect of the cardiac functional analysis is regional wall motion abnormality. All of these analyses rely upon the delineation (separation) of the contrast agent-filled blood from the ventricular myocardium. One method for cardiac function measurement using the multi-energy CT exams is outlined in FIG. 7. Application of the multi-energy analysis outlined in FIGS. 3 and 4 produce accurate delineation of the contrast-filled blood pool from the ventricular tissue as shown in FIG. 8. Once the ventricular mass is isolated at different phases of the cardiac cycle, detecting wall motion abnormality can be performed using any of the currently available methods.

Detection of Structural Changes

Myocardial tissue undergoes significant structural changes due to ventricular hypertrophy, hypertrophic cardiomyopathy, dilated cardiomyopathy and after myocardial infarction. For example, the ventricular wall thickens and becomes dense with severity of hypertrophy. In addition, the molecular composition of the myocardial tissue also changes with severity and duration of the disease as in cardiomyopathy where abnormal cells proliferate in between normal myocardial tissue. In myocardial infarction, tissue becomes necrosed and fibrous and eventually becomes thin and stretched and looses its contractility. In myocardial ischemia, lack of oxygenated blood alters the properties of the cardiac tissue and decreases the contractility of the ventricles.

As attenuation properties of the healthy myocardium and abnormal tissues (under abnormal conditions described above) for different X-ray energy levels are different, multi-energy CT system 10 provides the ability to diagnose these conditions accurately. After the ventricular chambers are separated from the images of the rest of the anatomy as explained in FIGS. 7 and 8, further analysis is performed using energy discrimination system 10 to detect, and diagnose these and similar diseases that affect the structure of the myocardium and point out possible therapeutic options. Examples of such diagnoses are shown in FIG. 9.

While the invention has been described in terms of various specific embodiments, those skilled in the art will recognize that the invention can be practiced with modification within the spirit and scope of the claims.

What is claimed is:

1. A method for obtaining data, said method comprising:
   scanning myocardial tissue of a patient with an Energy Discrimination Computed Tomography (EDCT) system to acquire data; and
   analyzing the acquired data for at least one of cardiac measurements, diagnosis, and prognosis after interventions.

2. A method in accordance with claim 1, wherein said scanning comprises scanning myocardial tissue to acquire perfusion data, said method further comprising determining at least one of a defect and a tissue viability based upon the acquired perfusion data.

3. A method in accordance with claim 2 wherein said scanning comprises generating a time-delayed series of cardiac images for measurement of perfusion levels in at least one part of a myocardium.

4. A method in accordance with claim 1 wherein said analyzing comprises analyzing the acquired data to determine a cardiac function.

5. A method in accordance with claim 4 wherein said analyzing comprises producing a delineation of a ventricular myocardium from a contrast-filled blood pool, wherein said producing comprises:
   separating at least one ventricle from anatomy surrounding the ventricle; and
   separating contrast-filled blood in the ventricle from ventricular tissue at at least one of an end diastole and an end systole.

6. A method in accordance with claim 1 further comprising separating soft plaque and calcified plaque from a contrast agent in a coronary artery.

7. A method in accordance with claim 1 further comprising detecting at least one structural defect in a heart muscle.

8. A method in accordance with claim 1 further comprising performing an automated bone segmentation.

9. A method in accordance with claim 1 wherein said analyzing comprises performing a Compton and photoelectric decomposition of the acquired data to differentiate abnormal regions of myocardial tissue from normal regions of myocardial tissue and delineate at least one of a contrast agent, a calcified plaque, and a bone from the myocardial tissue.

10. A method in accordance with claim 1 wherein said analyzing comprises performing a Basis Material Decomposition (BMD) of the acquired data to differentiate abnormal regions of myocardial tissue from normal regions of myocardial tissue and delineate at least one of a contrast agent, a calcified plaque, and a bone from the myocardial tissue.

11. An Energy Discrimination Computed Tomography (EDCT) System comprising:
   a radiation source;
   a radiation detector; and
   a computer coupled to said radiation source and said radiation detector, said computer configured to:
      acquire data regarding a first energy spectrum of a scan of myocardial tissue of a patient;
      acquire data regarding a second energy spectrum of the scan and
      analyze the acquired data for at least one of cardiac measurements, diagnosis and prognosis after interventions.

12. A system in accordance with claim 11, wherein said computer further configured to acquire myocardial perfusion data to determine at least one of a defect and a tissue viability based upon the acquired perfusion data.

13. A system in accordance with claim 12 wherein said computer further configured to generate a time-delayed series of cardiac images for measurement of perfusion levels in at least one part of a myocardium.

14. A system in accordance with claim 11 wherein said computer further configured to determine a cardiac function based upon the acquired data.

15. A system in accordance with claim 14 wherein said computer further configured to produce a delineation of a ventricular myocardium from a contrast-filled blood pool in the ventricle, wherein to produce a delineation, said computer is configured to separate at least one ventricle from anatomy surrounding the ventricle and separate contrast-filled blood in the ventricle from ventricular tissue at at least one of an end diastole and an end systole.

16. A system in accordance with claim 11 wherein said computer further configured to separate soft plaque and calcified plaque from a contrast agent in a coronary artery.

17. A system in accordance with claim 11 wherein said computer further configured to detect at least one structural defect in a heart muscle.

18. A system in accordance with claim 11 wherein said computer further configured to perform an automated bone segmentation.

19. A computer readable medium encoded with a program configured to instruct a computer to:
   receive data regarding a first energy spectrum of a scan of myocardial tissue of the patient;
   receive data regarding a second energy spectrum of the scan and
   analyze the acquired data for at least one of cardiac measurements, diagnosis and prognosis after interventions.

20. A computer readable medium in accordance with claim 19 wherein said program further configured to instruct the computer to:
   delineate a ventricular myocardium from a contrast-filled blood pool by:
      separating at least one ventricle from anatomy surrounding the ventricle; and
      separating contrast-filled blood in the ventricle from ventricular tissue at at least one of an end diastole and an end systole.

* * * * *